United States Patent [19]

Simonov et al.

[11] 4,067,887
[45] Jan. 10, 1978

[54] METHOD OF PREPARING DICHLOROMALEIC ANHYDRIDE

[76] Inventors: Vadim Dmitrievich Simonov, ulitsa Bljukhera, 18, kv. 38; Raif Timergalievich Gazizov, ulitsa Mira, 23, kv. 36; Vladimir Vadimovich Simonov, ulitsa Bljukhera, 18, kv. 38; Boris Ivanovich Voronenko, ulitsa Bljukhera, 48, kv. 9; Vera Vladimirovna Karpova, ulitsa Koltsevaya, 112, all of Ufa, U.S.S.R.

[21] Appl. No.: 713,967

[22] Filed: Aug. 12, 1976

[51] Int. Cl.$^2$ .......................................... C07D 307/60
[52] U.S. Cl. ........................... 260/346.74; 260/346.75
[58] Field of Search .................. 260/346.8 R, 346.8 A

[56] References Cited
PUBLICATIONS

Forsch et al., Chem. Ber. 106, pp. 1363–1364, (1973).

Primary Examiner—Natalie Trousof
Assistant Examiner—Bernard Dentz
Attorney, Agent, or Firm—Haseltine, Lake & Waters

[57] ABSTRACT

To prepare dichloromaleic anhydride, hexachlorobutadiene is subjected to oxidation with sulfur trioxide at a temperature ranging from 10 to 110° C in the presence of iodine or an iodine-containing compound such as an alkali metal iodide, whereafter the desired product is separated from the reaction mass.

The method of the present invention makes it possible to increase the yield of dichloromaleic anhydride up to 96% by weight, whereas in the prior art methods it is 80% by weight at most; the reaction time in the method according to the present invention is reduced by about 10 times as compared to that of the prior art methods.

5 Claims, No Drawings

METHOD OF PREPARING DICHLOROMALEIC ANHYDRIDE

The present invention relates to methods of preparing anhydrides of perchlorocarboxylic acids and, more specifically, to a method of preparing dichloromaleic anhydride.

The present invention may find extensive use in the production of self-extinguishing polyester resins and glass-fiber plastics; as a curing agent for epoxy resins, for the synthesis of efficient antiseptics used for protection of leathers, rubbers, paints and vulcanizates; in the production of herbicides fungicides and medicated compounds.

Numerous methods are known for the preparation of dichloromaleic anhydride, though the most effective are the methods contemplating oxidation of hexachlorobutadiene which is a by-product of the chlorination of hydrocarbons.

It is known that oxidation of hexachlorobutadiene with air oxygen containing 1% of chlorine at a temperature ranging from 140° to 210° C results in a series of oxidation products including about 1% of dichloromaleic anhydride.

This method has not been commercially implemented due to the production of a whole range of difficult-to-separate products and an insignificant yield of dichloromaleic anhydride.

Also known in the art is a method of preparing dichloromaleic anhydride involving oxidation of hexachlorobutadiene with chlorosulfonic acid or concentrated sulfuric acid in a current of chlorine at a temperature ranging from 150° to 190° C for a period lasting 10 to 30 hours.

The resulting homogeneous reaction mass is poured into water with ice, the unreacted hexachlorobutadiene is separated and recycled to the process, whereas dichloromaleic anhydride is recovered with ether and recrystallized from n-heptane by heating at reflux for a long period of time. The desired product yield reaches 76% as calculated for the reacted hexachlorobutadiene.

This prior art method has some disadvantages among which the most important are: long duration of the oxidation process (10 to 30 hours), the use of high temperatures; necessity of decomposition of the reaction mass with water, extraction of the resulting dichloromaleic anhydride with ether.

According to another prior art method, dichloromaleic anhydride is prepared by oxidation of hexachlorobutadiene with nitric acid.

The process is conducted in the following manner: hexachlorobutadiene is mixed with fuming nitric acid ($d^{20}_4 = 1.495$) and heated to a temperature of 90° C. Then, during a period of 40 hours the temperature is gradually elevated to 130° C, whereafter the reaction mixture is treated with concentrated sulfuric acid and maintained for 2 hours at a temperature of 170° C. resulting in a portion of the dichloromaleic anhydride being sublimed. The reaction mass is then cooled; the precipitated crystals of dichloromaleic anhydride are filtered off and dehydrated over phosphorus pentoxide. After a single sublimation at a temperature of 90° C under a pressure of 12 torr the desired product melting at 117°-118° C is obtained. The yield is about 70%. From the sulfuric-acid residue an additional amount of unseparated dichloromaleic anhydride is recovered by extraction with ether; this amount is about 11%.

This prior art method also has some essential disadvantages hindering its commercial implementation, i.e. the use of high temperatures which results in a partial sublimation of the resulting dichloromaleic anhydride, ethereal extraction; drying over phosphorus pentoxide; a high consumption rate of irreversibly lost nitric acid; high corrosion activity of the reaction medium.

Therefore, characteristic disadvantages inherent in the prior art methods of preparing dichloromaleic anhydride from hexachlorobutadiene involve: long duration of the process; insignificant yields; complicated technology for isolation of the desired product; complicated process scheme and equipment.

Accordingly, it is an object of the present invention to overcome the above-mentioned disadvantages.

It is an object of the present invention to provide a method which would ensure the production of increased amounts of dichloromaleic anhydride from a readily available raw material i.e. hexachlorobutadiene.

It is another object of the present invention to provide a method of preparing dichloromaleic anhydride which would feature a simplified process technology.

These objects are accomplished by effecting the oxidation of hexachlorobutadiene by means of sulfur trioxide at a temperature ranging from 10° to 110° C in the presence of iodine or an iodine-containing compound forming iodide ions under the reaction conditions, followed by isolation of the desired product from the reaction mass.

The present invention makes it possible to increase the yield of the desired product, i.e. dichloromaleic anhydride, up to 96% and simultaneously simplifying the process technology and providing an opportunity for commercial production of dichloromaleic anhydride.

It is advisable, in accordance with the present invention to effect distillation of the reaction mass in order to recover dichloromaleic anhydride by removing the fraction boiling at a temperature of not more than 138° C and cooling the residual mass to a temperature of 0° C, followed by filtration of the precipitated crystals of dichloromaleic anhydride, filter-washing and drying thereof.

The method according to the present invention makes it possible to avoid the use of low temperatures required for a complete recovery of dichloromaleic anhydride.

To ensure mild reaction conditions and obtain the yield of dichloromaleic anhydride as high as 96% at a degree of conversion of hexachlorobutadiene of 75%, iodides or iodates of alkali metals, chlorine or bromine iodides, alkyl or alkylene iodides, tetraalkylammonium iodide or iodides of aromatic compounds should be used as the iodine-containing compound.

To reduce the reaction duration by about 10 times as compared to that of the prior art methods of preparing dichloromaleic anhydride, it is advisable that iodine or the iodine-containing compounds be employed in an amount ranging from 0.05 to 1.5% by weight of the hexachlorobutadiene.

In accordance with the present invention, it is advisable to perform the oxidation at a temperature ranging from 30° to 60° C.

Owing to the present invention it has become possible to reduce the reaction temperature by 3 times thus enabling a high yield (up to 96% by weight) of the desired product.

Other objects and advantages of the present invention will now become more fully apparent from the following detailed description of the method of preparing dichloromaleic anhydride with reference to the examples illustrating the method of the present invention.

It has been found that oxidation of hexachlorobutadiene with a certain oxidizing agent under specified conditions can result in the formation of dichloromaleic anhydride with a yield of up to 96% by weight of the reacted hexachlorobutadiene and the desired product is recovered from the reaction mass by a conventional method. The method of the present invention imposes certain requirements on the reaction parameters involving the use of a specified catalyst, oxidizing agent and temperature ranges.

In accordance with the present invention, the process comprises oxidation of hexachlorobutadiene with sulfur trioxide in the presence of a catalyst. The catalyst can be iodine or any iodine-containing compound either organic or inorganic which forms, under the reaction conditions, iodide ions. The most suitable catalyst is iodine; besides, good yields of dichloromaleic anhydride are obtained with the use, as the catalyst, of iodides or iodates of alkali metals such as potassium iodide or potassium iodate; alkyl iodides such as methyl iodide, butyl iodide, dodecyl iodide; mixed halides such as iodine monochloride, iodine monobromide; tetralkylammonium iodides such as tetramethylammonium iodide; iodides of aromatic compounds such as iodobenzene, p-iodotoluene, o-iodotoluene.

The catalyst should be used in an amount ranging from 0.05 to 1.5% by weight of the hexachlorobutadiene employed. With a catalyst concentration below 0.05 wt.% a low conversion degree of hexachlorobutadiene is observed, while a catalyst concentration over 1.5 wt.% has no effect on the yield of dichlororomaleic anhydride or on the conversion of hexachlorobutadiene.

The sulfur trioxide employed for oxidation of hexachlorobutadiene may be introduced into the reaction zone either as it is or in the form of oleum. The concentration of the oleum exerts no effect on the oxidation of hexachlorobutadiene, but is desirable that 1 to 10 moles of sulfur trioxide be used per 1 mole of hexachlorobutadiene. Lesser amounts of sulfur trioxide supplied for the reaction will result in a decreased conversion of hexachlorobutadiene, whereas greater amounts (over 10 moles) of sulfur trioxide will result in a decreased yield of the desired product. The highest yield of dichloromaleic anhydride is obtained at a ratio of 3-4 moles of sulfur trioxide per 1 mole of hexachlorobutadiene.

The process of oxidation of hexachlorobutadiene can be effected within a wide range of temperatures, but in accordance with the present invention it is advisable that this process be conducted at a temperature within the range of from 10° to 110° C. At higher temperatures the catalyst is intensively carried away from the reaction zone and the process of oxidation of hexachlorobutadiene is sharply retarded. Furthermore, a parallel process of decomposition of dichloromaleic anhydride occurs (i.e. decarboxylation), whereby the yield of the desired product is lowered. At temperatures lower than 10° C, the reaction rate of hexachlorobutadiene oxidation is sharply decreased, whereby a low yield of the product with time is observed. It is preferable to conduct the oxidation of hexachlorobutadiene at a temperature within the range of from 30° to 60° C. In doing so, when the catalyst comprises iodine, alkyl iodides, iodides or iodates of alkali metals, mixed halides or any tetraalkylammonium iodide, it is preferable to carry out the oxidation process at a temperature of about 30° C, namely 30° to 45° C. When the catalyst comprises iodides of aromatic compounds, the process should be carried out at a temperature within the range of from 45° to 60° C.

To recover dichloromaleic anhydride from the reaction mass resulting from oxidation of hexachlorobutadiene with sulfur trioxide, the reaction mass is cooled to a temperature of −20° C. Therewith, dichloromaleic anhydride is precipitated in the form of white crystals which are filtered off and washed on the filter with a cooled solvent such as perchloroethylene, hexachlorobutadiene, n-heptane, and dried by conventional methods. Cooling to a temperature of −20° C is required to ensure a complete separation of dichloromaleic anhydride from the reaction mass. However, if the reaction mass is freed, by distillation, of compounds boiling below the temperature of 138° C (inorganic sulfur compounds) which readily dissolve dichloromaleic anhydride and hexachlorobutadiene, then a practically complete recovery of dichloromaleic anhydride is achieved upon cooling, to 0° C, the portion of the reaction mass left after the distillation. Dichloromaleic anhydride resulting from cooling is filtered off just as previously, washed on the filter with a cooled solvent and dried.

For a better understanding of the present invention some specific examples which, however, do not limit the scope of the invention, are given hereinbelow by way of illustration.

EXAMPLE 1

Into a four-necked flask provided with a thermometer, stirrer, relux condenser and bubbling means for the supply of sulfur trioxide there are charged 168 g (0.644 mole) of hexachlorobutadiene with 0.84 g iodine dissolved therein. The flask contents are heated to a temperature of 45° C and at this temperature 154 g (1.93 mole) of sulfur trioxide are passed therethrough. Then, the reaction mass is put into a distillation flask and the fraction boiling below 138° C is collected. The residue is cooled to 0° C. The precipitated crystals are filtered off, washed with perchloroethylene cooled to 0° C and dried to a constant weight to give 71.5 g (91.5% by weight) of dichloromaleic anhydride at a conversion of hexachlorobutadiene of 70%. The melting point of the resulting dichloromaleic anhydride is 120°–121° C.

EXAMPLE 2

Into a reaction flask provided with a thermometer, stirrer, reflux condenser and bubbling means for the supply of sulfur trioxide there are charged 168 g (0.644 mole) of hexachlorobutadiene and 0.084 g of iodine. The flask contents are heated to a temperature of 45° C and 154 g (1.93 mole) of sulfur trioxide are admitted thereinto during 2 hours. Thereafter, the reaction mixture is stirred for an additional 30 minutes and then cooled to a temperature of −20° C. The precipitated crystals are filtered off, washed, still on the filter, with perchloroethylene cooled to a temperature of from −10° to −25° C, and dried to a constant weight to give 46.6 g of dichloromaleic anhydride (87% by weight) at a conversion of hexachlorobutadiene of 48.8%. The melting point of the resulting dichloromaleic anhydride is 120° C.

EXAMPLE 3

Into the reaction flask described in the foregoing Example 1 there are charged 168 g (0.644 mole) of hexachlorobutadiene having dissolved therein 0.252 g of iodine. The flask contents are heated to a temperature of 90° C and at this temperature 257 g (3.21 moles) of sulfur trioxide are admitted thereinto during 3 hours with vigorous stirring. Thereafter, the reaction mixture is placed in a distillation flask with a dephlegmator and the fraction boiling below 138° C is distilled off. The residue is cooled to a temperature of from 0° to −10° C. The precipitated crystals are filtered off, washed with heptane cooled to the temperature of −20° C and dried to a constant weight to give 78 g (78% by weight) of dichloromaleic anhydride melting at a temperature of 119°–120° C, at a conversion of hexachlorobutadiene of 60%.

EXAMPLE 4

Into a reaction flask provided with a cooling jacket, reflux condenser, thermometer, stirrer and bubbling means for the supply of sulfur trioxide there are charged 168 g (0.644 mole) of hexachlorobutadiene having dissolved therein 0.084 g of iodine. By means of a thermostat a temperature within the range of 10°–12° C is maintained and at this temperature 154 g (1.93 mole) of sulfur trioxide are passed thereinto for 3 hours under constant stirring. The resulting dichloromaleic anhydride is recovered in accordance with the procedure described in Example 1 hereinbefore to give 27.7 g (87.5% by weight) of dichloromaleic anhydride melting at 119.5° C at a conversion of hexachlorobutadiene of 29.5%.

EXAMPLE 5

Into a reaction flask provided with a thermometer, stirrer and dropping funnel, there are charged 160 ml of hexachlorobutadiene and 2.5 g of iodine. To the thus-prepared solution there is added dropwise from a dropping funnel, 160 ml of 60% oleum during 2 hours. The reaction mass temperature is maintained within the range of from 40° to 45° C due to the reaction heat. Thereafter, the reaction mass is stirred for an additional hour at room temperature.

The resulting homogeneous reaction mass is poured onto ice; the precipitated crystals of dichloromaleic anhydride are filtered off, the remaining portion of dichloromaleic anhydride is recovered from the filtrate by means of ethereal extraction. The yield of commercial dichloromaleic anhydride is 94% (121 g of the theoretical value as calculated for the reacted hexachlorobutadiene. Conversion of hexachlorobutadiene is 75%, the melting point of the resulting dichloromaleic anhydride is 119° C.

EXAMPLE 6

The reaction is carried out in a manner similar to that described in Example 1 hereinbefore, except that the catalyst is methyl iodide ($CH_3I$) in the amount of 0.938 g. 58 g of dichloromaleic anhydride are obtained (a yield is 96% by weight) at the conversion of hexachlorobutadiene of 35.5%; the melting point of the product is 119° C.

EXAMPLE 7

The reaction is conducted in much the same manner as that described in the foregoing Example 1, with the exception that the catalyst is potassium iodate ($KIO_3$) in the amount of 1.415 g. The yield of dichloromaleic anhydride is 59.0 g (95% by weight) at a conversion of hexachlorobutadiene of 37%; the melting point of the product is 119° C.

EXAMPLE 8

The reaction is carried out in a manner similar to that described in Example 1 hereinbefore, with the exception that the catalyst is potassium iodide (KI) in the amount of 1.095 g. The yield of dichloromaleic anhydride is 56.6 g (89% by weight) at a conversion of hexachlorobutadiene of 38%; the melting point of the thus-obtained product is 119.5° C.

EXAMPLE 9

The reaction is carried out in accordance with the procedure described in the foregoing Example 1, with the exception that the catalyst is tetramethylammonium iodide $(CH_3)_4NI$ taken in the amount of 1.33 g. The yield of dichlororomaleic anhydride is 53.1 g (80% by weight) at a conversion of hexachlorobutadiene of 40%; the melting point of the resulting dichloromaleic anhydride is 119° C.

EXAMPLE 10

Into a reaction flask there are charged 66 g of the filtrate obtained in the foregoing Example 2 along with 0.3 g of iodine. The filtrate contains 95% by weight of hexachlorobutadiene, the remainder — inorganic sulfur-containing impurities.

The flask contents are heated to a temperature of 45° C and at this temperature 65 g (0.813 mole) of sulfur trioxide are passed thereinto for one hour. The reaction mass is further treated as in the foregoing Example 2 to give 41.5 g of dichloromaleic anhydride melting at a temperature of 119° C.

Example 11

The reaction is conducted in a four-neck flask provided with a thermometer, stirrer and dropping funnel, whereinto there are charged 250 g of commercial (96%) hexachlorobutadiene (0.958 mole) with 2.5 g of iodine dissolved therein. Then 76.6 g (0.958 mole) of sulfur trioxide are added dropwise thereto for one hour at a temperature of 110° C. The resulting crystals of dichloromaleic anhydride are recovered in a manner similar to that described in Example 1 hereinbefore. The yield of dichloromaleic anhydride is 112 g (70% by weight) at a conversion of hexachlorobutadiene of 25% (62.5 g). The melting point of the resulting dichloromaleic anhydride is 119° C.

EXAMPLE 12

A solution of hexachlorobutadiene in the amount of 26.1 g (0.1 mole) is charged into a reaction flask similar to that of Example 1 along with 0.39 g of the catalyst. 80 g (1.0 mole) of sulfur trioxide are then admitted into the flask for 2.5 hours at a temperature of 25° C. Separation of dichloromaleic anhydride is effected in a manner similar to that described in Example 1. The yield of dichloromaleic anhydride is 15.3 g (90% by weight); hexachlorobutadiene conversion is 11.3 g (45%). The melting point of the dichloromaleic anhydride is 120°–121° C.

EXAMPLE 13

The reaction is conducted as in Example 1, with the exception that the catalyst is iodobenzene ($C_6H_5I$) taken in the amount of 1.318 g. The yield of dichloromaleic anhydride is 37 g (87% by weight) at a conversion of hexachlorobutadiene of 40%. The melting point of the thus-prepared dichloromaleic anhydride is 119° C.

EXAMPLE 14

The reaction is conducted as in Example 1 hereinbefore, with the exception that the catalyst is p-iodotoluene ($C_6H_4CH_3I$) taken in the amount of 1.404 g. The yield of dichloromaleic anhydride is 39.5 g (88% by weight) at a conversion of hexachlorobutadiene of 42%. The melting point of the dichloromaleic anhydride thus prepared is 119.5° C.

EXAMPLE 15

The reaction is conducted as in Example 1 hereinbefore, with the exception that the catalyst is iodine monobromide (IBr) taken in the amount of 1.231 g. The yield of dichloromaleic anhydride is 62.85 g (91% by weight) at a conversion of hexachlorobutadiene of 65%. The melting point of the thus-prepared dichloromaleic anhydride is 119.5° C.

EXAMPLE 16

The reaction is conducted as in Example 1 above, with the exception that the catalyst is iodine monochloride (ICl) taken in the amount of 1.074 g. The yield of dichloromaleic anhydride is 69 g (93% by weight) at a conversion of hexachlorobutadiene of 70%. The melting point of the thus-prepared dichloromaleic anhydride is 120° C.

What is claimed is:

1. A method of preparing dichloromaleic anhydride comprising oxidizing hexachlorobutadiene with sulfur trioxide at a temperature ranging from 10° to 110° C in the presence of iodine or an iodine-containing compound forming iodide ions under the reaction conditions, followed by separating dichloromaleic anhydride from the reaction mass.

2. The method of preparing dichloromaleic anhydride as claimed in claim 1, wherein, for the separation of dichloromaleic anhydride, the reaction mass is subjected to distillation to remove the fraction boiling at a temperature of at most 138° C and the residual mass is cooled to 0° C, followed by filtration of the resulting crystals of dichloromaleic anhydride, filter washing and drying thereof.

3. The method of preparing dichloromaleic anhydride as claimed in claim 1, wherein the iodine-containing compound is selected from the group consisting of iodides and iodates of alkali metals, chlorine and bromine iodides, alkyl and alkylene iodides, tetramethylammonium iodide and iodides of aromatic compounds.

4. The method of preparing dichloromaleic anhydride as claimed in claim 3, wherein the iodine or the iodine-containing compound is employed in an amount ranging from 0.05 to 1.5% by weight of the hexachlorobutadiene.

5. The method of preparing dichloromaleic anhydride as claimed in claim 1, wherein the oxidation is conducted at a temperature ranging from 30° to 60° C.

* * * * *